(12) United States Patent
Bruder et al.

(10) Patent No.: US 7,860,209 B2
(45) Date of Patent: Dec. 28, 2010

(54) METHOD FOR IMAGING AN ORGAN, CONTROL DEVICE FOR A COMPUTED TOMOGRAPHY SYSTEM, COMPUTED TOMOGRAPHY SYSTEM AND A COMPUTER PROGRAM PRODUCT

(75) Inventors: Herbert Bruder, Höchstadt (DE); Rainer Raupach, Heroldsbach (DE)

(73) Assignee: Siemens Aktiengesellschaft, Munich (DE)

(*) Notice: Subject to any disclaimer, the term of this patent is extended or adjusted under 35 U.S.C. 154(b) by 217 days.

(21) Appl. No.: 12/000,831

(22) Filed: Dec. 18, 2007

(65) Prior Publication Data
US 2008/0165919 A1 Jul. 10, 2008

(30) Foreign Application Priority Data
Dec. 19, 2006 (DE) ............ 10 2006 060 482

(51) Int. Cl.
*H05G 1/62* (2006.01)
*G01N 23/083* (2006.01)
(52) U.S. Cl. ............................................. 378/8
(58) Field of Classification Search .......... 378/8, 378/4, 19, 95
See application file for complete search history.

(56) References Cited

U.S. PATENT DOCUMENTS

| | | | |
|---|---|---|---|
| 6,470,066 B2* | 10/2002 | Takagi et al. ............... | 378/8 |
| 6,560,309 B1* | 5/2003 | Becker et al. ............... | 378/8 |
| 6,708,052 B1* | 3/2004 | Mao et al. ................. | 600/407 |
| 6,763,082 B2* | 7/2004 | Ozaki ....................... | 378/8 |
| 6,836,529 B2* | 12/2004 | Li et al. .................... | 378/8 |
| 6,865,248 B1* | 3/2005 | Rasche et al. .............. | 378/8 |
| 6,937,690 B2* | 8/2005 | Bruder et al. .............. | 378/15 |
| 7,035,370 B2* | 4/2006 | Flohr et al. ................ | 378/8 |
| 7,251,308 B2* | 7/2007 | Tsuyuki .................... | 378/8 |
| 7,313,213 B1* | 12/2007 | Hsieh et al. ................ | 378/8 |
| 7,313,215 B2* | 12/2007 | Hsieh et al. ................ | 378/15 |
| 7,415,093 B2* | 8/2008 | Tkaczyk et al. ............. | 378/8 |
| 7,715,520 B2* | 5/2010 | Nagata et al. .............. | 378/8 |
| 2004/0077941 A1 | 4/2004 | Reddy et al. | |
| 2005/0058238 A1* | 3/2005 | Flohr et al. ................ | 378/8 |
| 2007/0153971 A1* | 7/2007 | Wang et al. ................ | 378/8 |
| 2007/0286331 A1* | 12/2007 | Keall et al. ................ | 378/8 |
| 2009/0310737 A1* | 12/2009 | Forthmann et al. ......... | 378/8 |

* cited by examiner

*Primary Examiner*—Edward J Glick
*Assistant Examiner*—Thomas R Artman
(74) *Attorney, Agent, or Firm*—Harness, Dickey & Pierce, P.L.C.

(57) ABSTRACT

A method is described for imaging an organ in a human or animal body via a computed tomography system having an X-ray radiation source which rotates around the body along a circumferential ring. In at least one embodiment, the circumferential ring in each case is fixed in one position for recording of an image data segment on one slice plane during one revolution of the X-ray radiation source relative to the body, and the X-ray radiation source is triggered by a cycle signal which represents a movement cycle of the organ and is activated for a limited measurement time interval. In at least one embodiment, the circumferential ring is moved sequentially to further positions relative to the body between each of the recordings, in order to record image data on further slice planes. In at least one embodiment, the timing and duration of the measurement time interval for an image data segment to be recorded are dynamically matched to a structure of the cycle signal. Furthermore, in at least one embodiment, a control device for a computed tomography system and/or a computed tomography system having a control device such as this are described.

19 Claims, 4 Drawing Sheets

METHOD FOR IMAGING AN ORGAN, CONTROL DEVICE FOR A COMPUTED TOMOGRAPHY SYSTEM, COMPUTED TOMOGRAPHY SYSTEM AND A COMPUTER PROGRAM PRODUCT

PRIORITY STATEMENT

The present application hereby claims priority under 35 U.S.C. §119 on German patent application number DE 10 2006 060 482.2 filed Dec. 19, 2006, the entire contents of which is hereby incorporated herein by reference.

FIELD

Embodiments of the invention generally relate to a method for imaging an organ in a human or animal body. In at least one embodiment, this may be done, for example, by way of a computed tomography system including an X-ray radiation source which rotates around the body along a circumferential ring, with the circumferential ring in each case being fixed in one position for recording of an image data segment on one slice plane during one revolution of the X-ray radiation source relative to the body, and with the X-ray radiation source being triggered by a cycle signal which represents a movement cycle of the organ and being activated for a limited measurement time interval and with the circumferential ring being moved sequentially to the desired further positions along the body relative to the body between each of the recordings in order to record image data on further slice planes.

Furthermore, at least one embodiment of the invention generally relates to a control device for a computed tomography system such as this, which has a signal input for inputting an appropriate cycle signal and is designed such that it operates the computed tomography system in the manner described above. At least one embodiment of the invention also generally relates to a corresponding computed tomography system having a control device such as this, and to a computer program product which can be loaded into a memory of a control device of a computed tomography system in order to carry out the method.

BACKGROUND

In modern medicine, non-invasive or minimal invasive methods are widely used for organ imaging. The aim of these methods is essentially to obtain detailed knowledge about the respective organ and its state without opening the body. In the computed tomography system mentioned initially, three-dimensional images of the interior of an object that is being examined are produced using an X-ray method. For this purpose, an X-ray radiation source rotates, as described, very quickly along a circumferential ring (normally in a so-called gantry housing) around the body of the patient, and passes radiation through the body during the process. A detector is in each case located opposite the X-ray radiation source and detects the X-rays, which have been attenuated by the body, on a position-resolved basis. Two-dimensional X-ray slice images can then be reconstructed from the image data recorded by the detector device, from which, finally, slice images and a three-dimensional image can be reconstructed.

In computed tomography, a fundamental distinction is drawn between two recording methods. In one method, the gantry is moved continuously forwards around the body in the longitudinal direction of the body relative to the patient (referred to in the following text as the z-direction) while the X-ray radiation source is being rotated, so that the X-ray radiation source revolves around the body in the form of a helix throughout the entire examination. This method is normally referred to as spiral scanning. A further method is so-called "sequential scanning", as has already been mentioned in the introduction. In this case, the circumferential ring is kept at a fixed position while recording a specific slice plane.

Once the slice image has been completed at this position, then the circumferential ring is subsequently moved to the new position relative to the body, and a new recording is thus produced in an adjacent slice plane. In this case, the expression a relative movement of the circumferential ring with respect to the body of the patient is intended in the following text to mean not only a movement of the circumferential ring with respect to a patient whose position is fixed in space on an examination table or the like but also—as in the case of most equipment—a movement of the patient, with an examination table which can be moved by the circumferential ring in the z-direction, with a gantry housing being fixed in space.

In many cases, the spiral scanning method is used nowadays, with the X-ray emitter generally emitting continuously during the forward movement. On the other hand, this method, which necessarily results in a large overlap of image data and in which in consequence the tissue must also be irradiated more than once, leads to larger doses being applied. On the other hand, the sequential method has the advantage that a dose is in principle applied only when a recording is also actually being made of one specific slice image plane. In this case, at least half a revolution plus the beam angle resulting from the beam geometry of the X-ray beam are required for reconstruction, with the beam angle generally being in the order of magnitude of 50°.

In practice, a transition angle of about 30° is normally additionally used in order to avoid artifacts at the interfaces of the projection angle interval. In order to improve the time resolution and thus to improve the image quality, it is also possible for a segment such as this to be composed of segment elements, for example of two segments each having only one quarter of the rotation (in each case plus the equipment-dependent beam angle), which are recorded at the same examination table position.

However, one problem with all of these methods is to record organs which move rapidly. Specifically, the only image data which can be used for a sensible image reconstruction is that which in each case shows the organ in the same state. In one of the most important applications, heart recording, the filling phase or diastole is in this case preferably chosen as a phase in which the heart is relatively at rest, for display purposes. With a living human, this rest phase lasts for less than 100 ms, even when relaxed in a resting position. In consequence, only image data within a limited measurement time interval, at a time within this rest phase, can be used for image reconstruction. However, in addition, there are also specific recordings in which the heart is in fact intended to be recorded in the systolic phase, that is to say in maximum contraction.

At the moment, most cardiac CT examinations (heart computed tomography examinations) are carried out using a spiral recording process, with the recorded image data being selected (gated) retrospectively. For this purpose, an EKG of the patient is recorded at the same time, in parallel with the computed tomography recording. The permissible measurement time intervals within the respectively desired heart phases are determined on the basis of this EKG signal. The only image data which is then used for reconstruction is that originating from these permissible measurement time intervals. All the other data is generally ignored for image reconstruction of the heart. Although these examination methods have the advantage of a relatively short examination time, their disadvantage is a high dosage application.

In order to reduce the dose at least somewhat, spiral scanning methods are already currently in use, in which the tube current for the X-ray radiation source is modulated correlated with an EKG signal, with the dosage thus being reduced to approximately 20%, for example, in specific phases in which the heart definitively cannot produce any recordings that could be assessed. This remaining dose is just sufficient in order to use the image data obtained in this way for reconstruction if necessary, provided that no suitable image data is available from a spatial direction that is required for complete reconstruction.

In contrast, with the broad multi-row detectors which have recently become available and have a plurality of detector rows in the z-direction, sequential scanning methods are also now of interest for cardio-CT examinations. In order to ensure for this purpose that the dose is as low as possible, it is highly worthwhile triggering the recording with the aid of a cycle signal which represents the movement cycle of the organ, for example with the aid of the EKG signal in the case of a heart recording. The EKG can then be used to define the next measurement time interval, so that radiation is applied only within this time interval. However, this method has the disadvantage that it works sufficiently well only if the EKG is highly uniform. In most cases, however, the heart rate varies during recording.

In addition, arrhythmic movements of the heart also frequently occur. This is because the patient is virtually unavoidably in a stress situation during the measurement, and in fact these are generally patients who are actually being investigated because their heart behavior is abnormal.

In none of these cases is it certain that the measurement time interval defined in advance on the basis of the heart rate will adequately match the phase of the heart to be recorded. This can be determined only while the recording is actually being made. This means that it is not possible to decide until after an X-ray dose has been applied whether this was justified at all and whether the image data measured immediately before this can be assessed.

In general, particularly in the case of patients with arrhythmic EKGs, much of the data is therefore rejected, so that the dose was admittedly applied, but was not used. In the end, this then leads on the one hand to the examination times being longer than in the case of traditional spiral scans and the radiation dose in fact coming close to that of spiral scans, because of the recordings which cannot be used. For this reason, dose-reducing sequential scanning is generally not used—except in the case of patients with a very rhythmic EKG, and spiral scanning is carried out instead of this.

In order to keep the unnecessarily applied dose as small as possible, US 2004/0077941 A1 proposes a method which, inter alia, can also be used for a helical scan, and in which an EKG of the patient is recorded in advance during a test phase. This EKG is analyzed in order to find a plurality of successive "normal" QRS complexes. A representative QRS complex, and therefore a representative RR interval for the patient, are then determined on the basis of these QRS complexes. The length of a measurement time interval which will normally fit well into a desired phase of the representative QRS complex is then defined with the aid of the representative RR interval.

During a subsequent computed tomography measurement, an EKG which is recorded at the same time is used to determine whether this has any discrepancies from the representative QRS complex, in order in this way to detect arrhythmia. If an arrhythmia is detected during a measurement time interval, then the X-ray tube is switched off prematurely, and the measurement data is rejected. The process then waits for the next suitable QRS complex into which the defined measurement time interval fits. However, if the EKG is highly arrhythmic, this unfortunately also leads to a very long measurement time and to a large number of irradiation time periods which cannot be used, although they are shorter.

SUMMARY

In at least one embodiment of the present invention, a method, a control device for a computed tomography system, a computed tomography system and/or a computer program product for a control device for a computed tomography system are disclosed such that it can also be used in a worthwhile manner for cycle signals which are subject to major variations.

In the method according to at least one embodiment of the invention, as in the case of a typical sequential scan, the circumferential ring is fixed in one position relative to the body in order to record image data on a specific slice plane, and, triggered by a cycle signal which represents the movement cycle of the organ, the X-ray radiation source is activated for a limited time interval while it is being moved along a specific segment of the circumferential ring. In this case, activation means that the X-ray radiation source is switched on to such an extent that it produces adequate radiation for image reconstruction. Thus, the X-ray radiation source is deactivated in this sense at the other times outside the measurement time interval, that is to say it is effectively switched off completely, or may continue to run with a greatly reduced dose.

Between the recordings on different slice planes, the circumferential ring is then moved sequentially to the desired further positions relative to the body, either with the patient being kept fixed in space and the circumferential ring being moved, or being fixed in space and the patient being moved in the z-direction on the examination table.

According to at least one embodiment of the invention, in this case, the timing and duration of the measurement time interval for an image data segment to be recorded are dynamically matched to a structure of the cycle signal at that time. The respective structure at that time is in this case determined from the current or the previous measurement cycle, and from any desired number of previous measurement cycles. These can each be used to determine the timing and the duration of the next measurement time interval. A structure of the cycle signal is in this case defined by specific structural features such as the mean frequency, variation, variance, trend or other characteristics or special features. In this case, various rules can be used to determine the next measurement time interval on the basis of this structure data. Examples of suitable rules will be explained in the following text, as well.

The method according to at least one embodiment of the invention therefore results in the measurement time interval being estimated individually as appropriately as possible for the next image data segment to be recorded. In this case, the measurement time interval can also be changed spontaneously if it is found that the actual structure of the subsequent signal cycles does not appear in the same way as was estimated when the measurement time interval was determined on the basis of the actual structure at that time.

The method according to at least one embodiment of the invention admittedly leads to longer measurement time intervals, which in turn leads to a somewhat greater dosage application, in comparison to a method in which, for example, the measurement time interval was defined once at the start as a function of the average frequency of the cycle signal. However, this is more than compensated for by the fact that image data which can be assessed is produced from virtually all the measurement time intervals, and unnecessary repetitions of measurements are avoided. In particular, it should be remembered that this method can also be used for highly arrhythmic cycle signals and there is therefore no need to make use of conventional spiral scanning methods with a much higher dose. Overall, a considerable reduction in the dose for such examinations is achieved by this method.

A control device according to at least one embodiment of the invention for a computed tomography system requires, as in the past, a signal input for inputting the cycle signal. This control device must be designed such that it operates the computed tomography system such that the circumferential ring is in each case fixed relative to the body of a patient for a recording of an image data segment on a slice plane during one revolution of the X-ray radiation source, and the X-ray radiation source is activated, triggered by the cycle signal, for a limited measurement time interval, and such that the circumferential ring is in each case moved sequentially to the desired further positions along the body between each of the recordings, in order to record image data on further slice planes. In addition, according to the invention, the control device must have a measurement time interval determining unit which dynamically matches the timing and duration of the measurement time interval for an image data segment to be recorded to a structure of the cycle signal.

A control device such as this can in this case be used with any desired computed tomography system provided that an appropriate appliance is available for measurement of a suitable cycle signal, for example an EKG appliance. Since the measurement time interval determining unit may also be in the form of a software module, it is advantageously also possible to configure an existing control device, in which appropriate software is already installed for controlling the computed tomography system as a function of cycle signals such as these, by way of a simple update, according to at least one embodiment of the invention.

In principle, at least one embodiment of the invention can be used for all types of computed tomography systems, that is to say both for systems in which an X-ray radiation source is used with a stationary detector array extending completely along the circumferential ring, and for computed tomography systems with detector arrays in the form of circle segments, which revolve in synchronism with the X-ray radiation source.

It is likewise possible to the use at least one embodiment of the invention for a so-called dual-source computed tomography system, that is to say a system with two X-ray emitters and, possibly, two detectors, or for a computed tomography system with an even greater number of X-ray emitters and/or detectors. Furthermore, it can also be used for electron-beam tomography.

In one method, in at least one embodiment, the measurement time interval for a subsequent measurement is formed from a minimum time interval, which depends on the rotation rate of the X-ray radiation source and an angle range to be covered, and on a variable safety time interval, which is dependent on the structure of the cycle signal. This necessarily ensures that the measurement time interval is always sufficiently long to allow the desired data segment to be recorded at all. In addition, the safety time interval considerably increases the probability of the organ also being in the phase which is intended to be recorded within the measurement time interval.

In this case, the safety time interval is preferably in each case chosen for the subsequent measurement as a function of the variability of the cycle signal at that time. This means that the safety time interval is determined using parameters which depend on how variable the cycle signal was at that time or in a specific number of previous signal cycles.

In order to define a start time for a subsequent measurement time interval, it is particularly preferable to estimate the time when a specific characteristic feature will occur for the next time in the cycle signal. This estimation process is carried out on the basis of the profile of previous signal cycles. For example, in the case of an EKG, the occurrence of the next R-peak may be estimated, since this R-peak occurs significantly in each EKG and is therefore particularly highly suitable for use as a characteristic feature.

Both the definition of the variable safety time interval and the estimate of the time of the next occurrence of the specific characteristic feature can be produced as a function of a mean value and/or a median of the cycle length of a number of previous cycles.

In the same way, one or more of the following parameters can preferably be used for this estimation process:
 minimum cycle length of a number of previous cycles,
 maximum cycle length of a number of previous cycles,
 trend line of a number of previous cycles, and
 standard deviation (for example with the mean value also normalized) of the trend line of a number of previous cycles.

The consideration of the minimum and maximum cycle length and of the trend line and the standard deviation as well makes it possible to produce a particularly good estimate as a function of the variability of the cycle signal at that time while, in contrast, estimation solely as a function of a mean value or of a median takes account only of the variation of the frequency.

In this case, the same number of previous cycles may in each case be used to determine the mean value or the median as well as the minimum cycle length, the maximum cycle length, the trend line, standard deviation of the mean value or of the median. However, it is also possible to define a specific number of previous cycles for each of these parameters, to be taken into account for the determination of this parameter.

The safety time interval particularly preferably has a predeterminable minimum length which may be predetermined by the operator as required for this function, or else in the factory. This method is equivalent to a method in which at least one predeterminable fixed safety time interval is first of all added to the minimum time interval, followed by a further variable safety time interval, which in turn should depend on the variability of the cycle signal at that time.

The method, in at least one embodiment, should also advantageously take account of suddenly occurring random events such as an additional or premature occurrence of a new cycle or a delayed cycle. Typical examples of events such as these in an EKG are so-called extrasystoles or delayed cycles in which the R-peak occurs abnormally late, and the cycle therefore lasts for a very long time.

In one example embodiment of the method, when a specific characteristic feature occurs, for example the R-peak in the EKG, image data recording is therefore terminated while recording an image data segment. In this case, it is irrelevant whether this relevant characteristic feature occurs prematurely. Since no image data that can be assessed can be acquired in any case in the rest phase during the R-peak in an EKG for a cardio-CT examination, it is worthwhile terminating the image data recording at this time, in order to avoid unnecessary dosage application.

Furthermore, in some cases in which a specific characteristic feature occurs prematurely, that is to say before the estimated time period of the next occurrence, it may be preferable to start image data recording immediately. By way of example, this allows image data to be recorded after an extrasystole, as well. Conversely, if the feature does not occur in the estimated time period of the next occurrence of the specific characteristic feature, the recording of an image data segment is started from a specific time which, for example, may be located at the end of the estimated time period or else shortly after it. This measurement time interval is then terminated again when the specific characteristic feature actually occurs or at the latest when the calculated measurement time interval has ended.

As already explained in the introduction, in the case of a sequential method it is possible to record a plurality of short segments rather than one long image segment in order to improve the time resolution at one position. A check is therefore preferably carried out after recording an image data segment to determine whether a further image data segment should be recorded at the present position. In this case, a check is carried out on the basis of predetermined rules to determine whether the recording of an image data segment such as this is absolutely essential in order to allow an adequately good image to be reconstructed at all on this slice image plane, and/or a check is carried out to determine whether further recording of an image data segment in this way is worthwhile at least to allow the time resolution on this slice image plane to be improved. If this is the case, then the further image data segment recording is carried out at the same position, otherwise the process moves to the new position.

As mentioned, the method is particularly advantageous for heart recording. An EKG signal is therefore preferably used as the cycle signal. Furthermore, the method may, however, also be used for recording other cyclically moving organs. If this movement is influenced by the heart movement, for example because these are organs immediately adjacent to the heart which are also moved with the heart movement, the EKG signal can also be used as the cycle signal for recordings such as these.

BRIEF DESCRIPTION OF THE DRAWINGS

The invention will be explained in more detail in the following text once again with reference to the attached figures and using example embodiments. In the figures.

DETAILED DESCRIPTION OF THE EXAMPLE EMBODIMENTS

Figure 1:
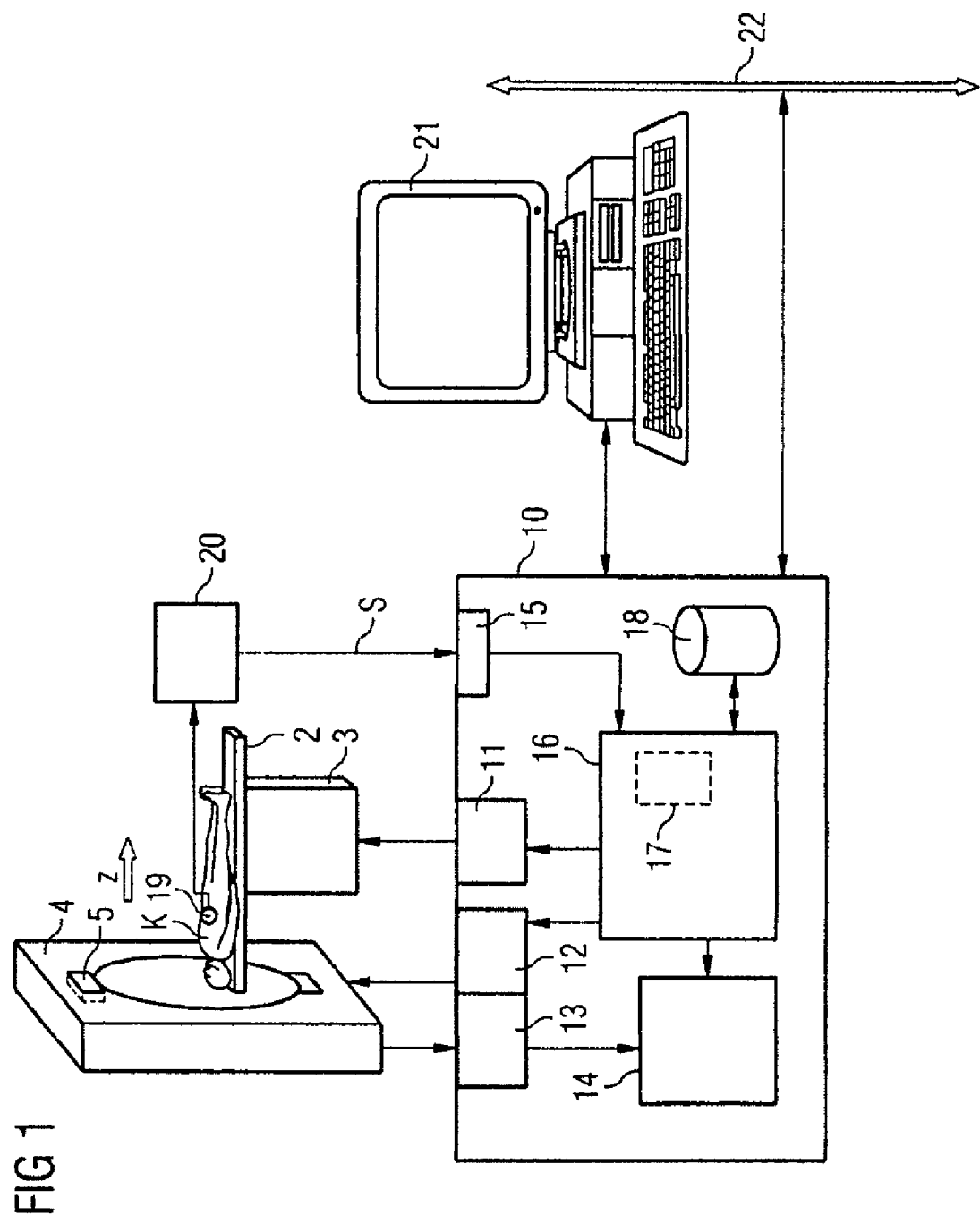
FIG. 1 shows a schematic illustration of one example embodiment of a computed tomography system according to an embodiment of the invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

The following text is based on the assumption, without embodiments of the invention being restricted to these, that the CT recording is a cardio-CT examination in which the aim is to record the patient's heart in the rest phase. In this case, the EKG signal S of the patient recorded during the CT examination is used as the cycle signal S.

The computed tomography system 1 illustrated in FIG. 1 is an intrinsically commercially available computed tomography system whose control device 10, as will be explained in more detail in the following text, has been modified in the manner according to an embodiment of the invention in order to produce a computed tomography system according to an embodiment of the invention.

The computed tomography system 1 has a conventional scanner with an X-ray radiation source 5 which rotates quickly along a circumferential ring 4. A detector (not illustrated) revolves in synchronism with the X-ray radiation source 5 on the circumferential ring 4 on the respectively opposite side of the X-ray radiation source 5, with this detector preferably being a broad multi-row detector. The body K of the patient is on an examination table 2 which is mounted on a subframe 3 such that it can be moved in the longitudinal direction through the circumferential ring 4. For this purpose, the subframe 3 is equipped as an appropriate movement device 3 with motors etc, so that the body of the patient can be moved completely through the circumferential ring 4 once in z-direction.

This scanner is operated by way of a control device 10. The X-ray radiation source 5, for example a traditional X-ray tube with an associated X-ray generator (not illustrated), as well as all the other equipment required such as motors for movement of the X-ray radiation source 5 and of the detectors along the circumferential ring 4 and for movement of the examination table 2, can be operated, inter alia, via the control device 10. This control device 10 has a first interface 11, via which the movement device 3 for the examination table 2 can be operated, in order to position the body K of the patient relative to the circumferential ring 4. Furthermore, the control device 10 has an interface 12 via which the X-ray radiation source 5 (and the X-ray generator) as well as the speed of revolution of the X-ray radiation source 5 are controlled. The raw image data coming from the detector is read via a further interface 13. The raw image data is then passed to a reconstruction unit 14, which reconstructs the images.

A central component within the control device 10 is a measurement procedure control unit 16. This ensures that the X-ray radiation source 5, the detector, the drive motors in order to rotate the components and the driver for the examination table 2 are operated in accordance with predetermined measurement protocols. Measurement protocols such as these may, for example, be stored in a memory 18. Furthermore, the measurement protocols may be varied and adapted by an operator via a terminal 21 which is used to control the entire computed tomography system 1. New protocols can likewise be predetermined via the terminal 21. The images produced by the reconstruction unit 14 can also be output on the screen of this terminal 21.

The control device 10 is also connected to a bus system 22, to which further components can be connected, such as bulk image memories, further image computers, filming stations, etc. Measurement protocols can likewise be loaded, or loaded measurement protocols can be transmitted, via this bus system 22. It is likewise also possible to transmit the raw image data acquired by way of the interface 13 via the bus system 22 to an external reconstruction unit, where the images are actually reconstructed.

The measurement procedure control unit 16 is in this case designed such that, assuming that appropriate protocols have been predetermined, it can carry out sequential measurements, in which, as already described in the introduction, slice images of the patient are produced at various fixed positions, and the position of the patient relative to the circumferential ring 4 is varied sequentially between the individual slice image recordings. It is, of course, also possible for the measurement procedure control unit 16 to operate the scanner in order to carry out a spiral scanning process, provided that this has been predetermined by appropriate protocols.

In order to carry out a sequential cardio-CT examination, the measurement procedure control unit 16 is, according to an embodiment of the invention, equipped with a measurement time interval determining unit 17 which, for example, may be in the form of suitable software within the measurement procedure control unit 16. For a sequential measurement of a cyclically moving organ, this measurement time interval determining unit 17 individually and dynamically determines the timing and duration of the measurement time interval for an image data segment to be recorded subsequently, depending on the structure of the current EKG of the patient. For this purpose, the control device has a signal input 15 to which an EKG appliance 20 can be connected and produces the EKG signal S. The EKG appliance 20 has electrodes 19 which are positioned in the normal manner on the body K of the patient during the measurement.

The way in which the measurement time interval determining unit 17 determines a subsequent measurement time interval will be explained in the following text with reference to FIGS. 2 to 4.

The entire computed tomography system 1 further also has all the other normal components and features of known computed tomography systems. However, these are not illustrated in FIG. 1, for the sake of clarity.

Figure 2:
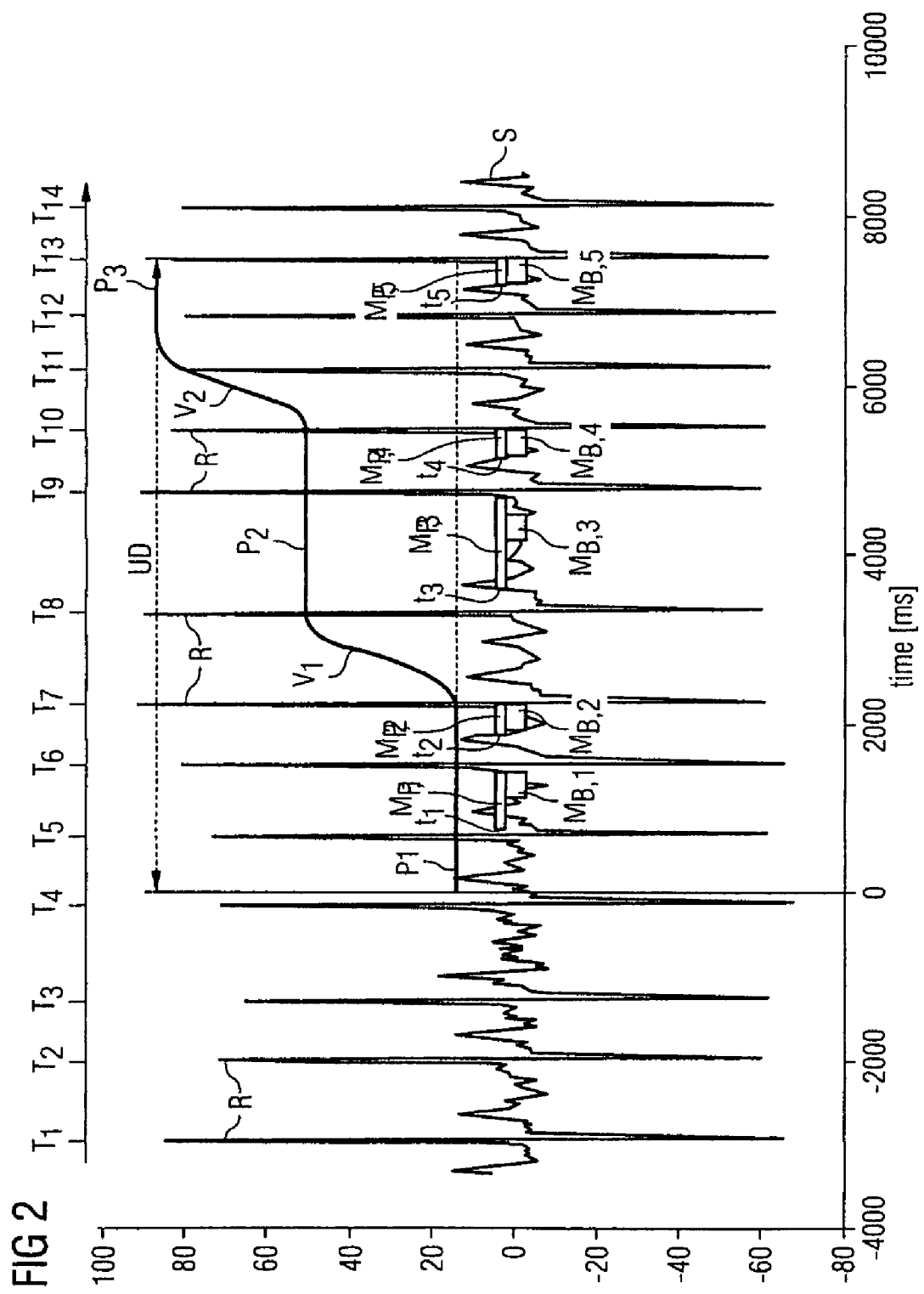
FIG. 2 shows one example of an EKG with measurement time intervals marked in it which have been defined with the aid of the method according to an embodiment of the invention.

FIG. 2 shows a typical example of an EKG with irregularities. In this case, the reference symbols $T_1, T_2, \ldots, T_{14}$ are used to mark each of the times at which the R-peak occurs in the EKG, with this being evident as a particularly significant feature R and therefore being particularly highly suitable for identification of a cycle. The illustration also shows a curve, illustrating the positioning of the circumferential ring 4 relative to the body K of the patient at three positions $P_1, P_2, P_3$ during an examination period DU. In reality, an examination such as this may possibly include more measurements at a large number of positions, depending on the length of the volume to be examined, and on the detector width. A measurement over only three positions $P_1, P_2, P_3$ is illustrated here, just for simplicity.

The examination table is in each case moved relative to the circumferential ring 4 between the positions $P_1, P_2, P_3$ along the sections $V_1, V_2$.

This figure shows the measurement time intervals $M_{B,1}$, $M_{B,2}, M_{B,3}, M_{B,4}, M_{B,5}$ within the EKG which are in each case at least required in order to record a data segment required for reconstruction. In addition, the graph shows the measurement time intervals $M_{P,1}, M_{P,2}, M_{P,3}, M_{P,4}, M_{P,5}$ in each case determined in advance with the aid of the method according to an embodiment of the invention.

In an embodiment of the method described here, both the length of the measurement time intervals $M_{P,1}, M_{P,2}, M_{P,3}, M_{P,4}, M_{P,5}$ and their starting times $t_1, t_2, t_3, t_4, t_5$ are defined using the following procedure:

First of all, in a first step at the start of the measurement, the position $T_5$ of the next R-peak is estimated, and the subsequent measurement time interval $M_{P,1}$ is calculated on the basis of this estimate and the minimum time interval required for reconstruction. Established methods may be used in this case, such as those used for EKG-correlated tube current modulation for spiral scanning. However, it is preferable to ensure that the complete structure of the EKG, that is to say its variance, trend, etc. is taken into account and not just, for example, the mean heart rate over the most recent cycles. This increases the confidence that the prospectively required heart phases will also actually be covered by the measurement time interval $M_{P,1}$.

Figure 3:
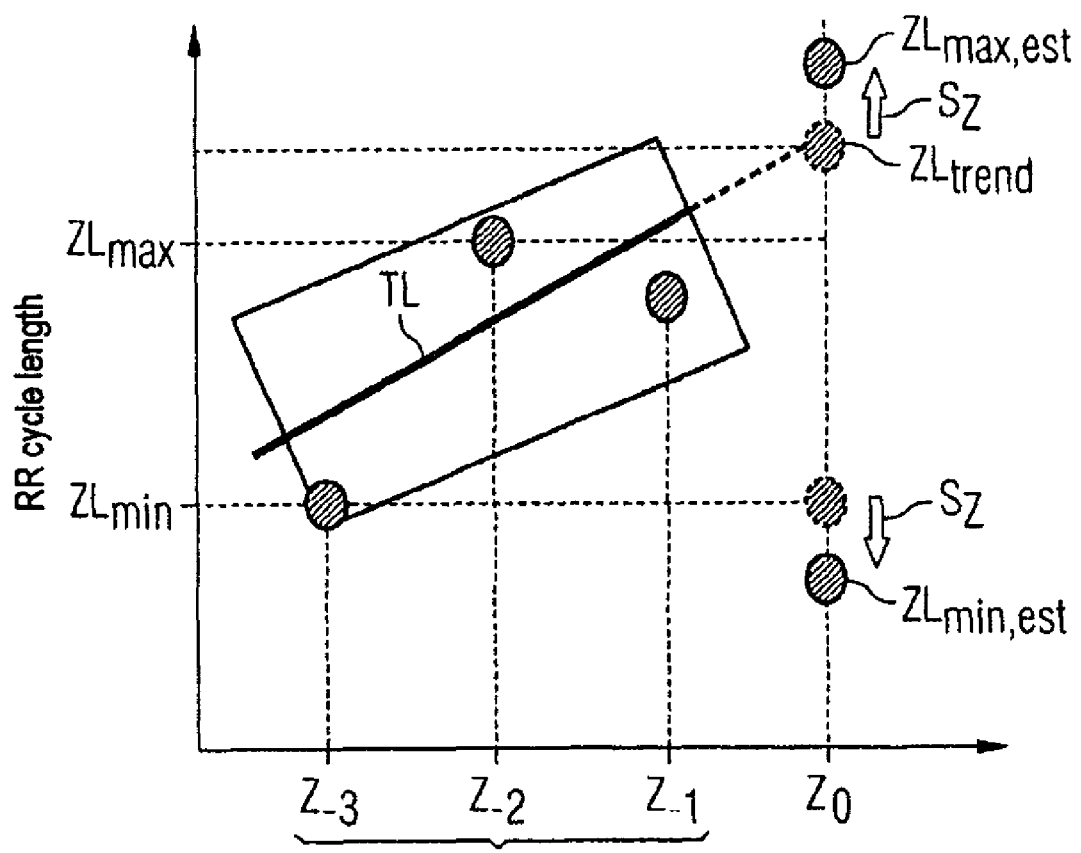
FIG. 3 shows a graph in order to illustrate one possible method for estimation of a subsequent measurement time interval.

FIG. 3 shows, in the form of a graph, how an estimate such as this of the position of the next R-peak can advantageously be produced on the basis of the previous cycles in order to have an adequate confidence range. In this case, the cycle length to be expected in the current cycle $Z_0$ from the last R-peak to the next subsequent R-peak is estimated. This is done by using the last three previous cycles, which are annotated $Z_{-3}, Z_{-2}, Z_{-1}$ in FIG. 3. The graph in each case shows the cycle length, that is to say the time interval between the respective two adjacent R-peaks, over the cycles $Z_{-3}, Z_{-2}$, $Z_{-1}$. On the one hand the minimum cycle length $ZL_{min}$ and the maximum cycle length $ZL_{max}$ and on the other hand the trend line TL as well, which is obtained for example by linear regression from the cycle lengths of the last three cycles $Z_{-3}$, $Z_{-2}$, $Z_{-1}$, are taken into account in order to estimate the next cycle and the timing of the next R-peak. Taking account of this trend line TL, extension to the next cycle $Z_0$ to be estimated results in a cycle length $ZL_{Trend}$ which is somewhat above the maximum cycle length $ZL_{max}$. The maximum of $ZL_{max}$ and $ZL_{Trend}$ is used as a provisional estimate for the maximum cycle length (maximum estimate), and the minimum of $ZL_{min}$ and $XL_{Trend}$ is used as an estimate for the minimum cycle length (minimum estimate).

Depending on the fluctuations in the heart cycle length, that is to say the discrepancies from the trend line, a safety time margin $S_z$ is also subtracted from the minimum estimate and/or added to the maximum estimate in order in this way to arrive at a maximum value $ZL_{max,est}$ and a minimum value $ZL_{min,est}$ for the estimated cycle length. The safety time margin is preferably chosen to be proportional to the standard deviation of the three cycles $Z_{-3}$, $Z_{-2}$, $Z_{-1}$ from the trend line TL. These estimates result in a time interval in which the next R-peak $T_6$ is expected to occur. On this basis, the next measurement time interval $M_{P,1}$ can then be planned taking into account the normal position of the rest phase relative to the R-peak and the minimum required length of the measurement time interval for recording the required segments. Both the maximum values and the minimum values of the cycle lengths, the trend and the variation in the EKG are taken into account by this calculation process, that is to say automatically, in this planned measurement time interval $M_{P,1}$, so that the planned measurement time interval $M_{P,1}$ covers the minimum necessary measurement time interval $M_{B,1}$.

Data recording is then carried out during the planned measurement time interval $M_{P,1}$ from the start time $t_1$, and the X-ray radiation source is appropriately activated. At the moment that the next R-peak is measured at the time $T_6$, it is then possible to retrospectively calculate the measurement time interval which would actually have been required. If required, data recording is then therefore ended immediately, even if the intrinsically planned measurement time interval $M_{P,1}$ should have been longer.

The position of the next R-peak $T_7$ is then estimated once again using the method described above. The known length of the cycle that has now passed and the estimated next length can be used to assess whether this is an abnormal cycle resulting, for example, from an extrasystole or which was significantly longer than a predetermined comparison cycle length, for example as the average cycle length. A check is likewise carried out to determine whether an adequate data segment has been recorded or whether rerecording at this position is necessary, or whether the current heart rate allows the time resolution to be improved by a multi-segment method. In this case, if required, a further, generally short, data segment is recorded once again at the same position, and is used in addition to the first data segment for reconstruction in order in this way to obtain a better slice image of this slice plane, overall.

If this is the case, then the next measurement time interval $M_{P,2}$ is calculated. This is done using the already described method on the basis of the already estimated current cycle length. As soon as the start time $T_2$ of this next planned measurement time interval $M_{P,2}$ is reached, another measurement starts at the same position. This is terminated again on reaching the next R-peak $T_7$. As shown in FIG. 2, the actual required measurement time interval $M_{B,2}$ is also covered very well in this case.

The examination table is then moved to the next position $P_2$ during the time period $V_1$, although this may take longer than one heart cycle, depending on the movement distance.

The timing $T_9$ of the next occurrence of the R-peak is then estimated first of all in the manner described above at the new position $P_2$, and a planned measurement time interval $M_{P,3}$ is calculated on this basis. In this case well, it is likewise possible to check whether there is any point in recording further segments, and correspondingly further measurement time intervals $M_{P,4}$ may be planned and measurements carried out. Finally, a further method is carried out in the time period $V_2$ relating to the position $P_3$ etc until, finally, the complete measurement has been carried out.

Figure 4A:
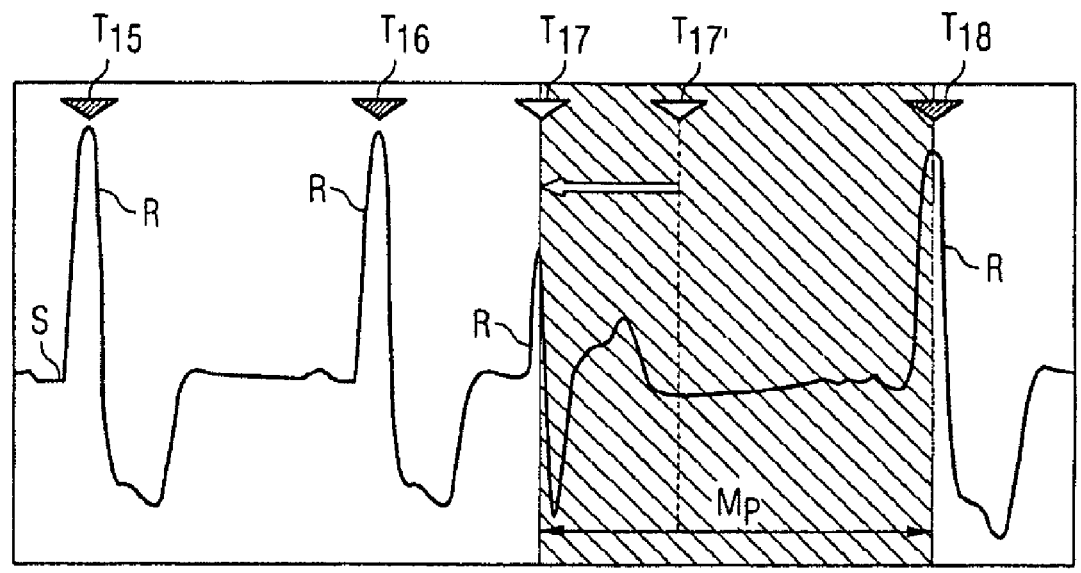
FIG. 4a shows a schematic illustration of a measurement time interval within an EKG with an extrasystole.
Figure 4B:
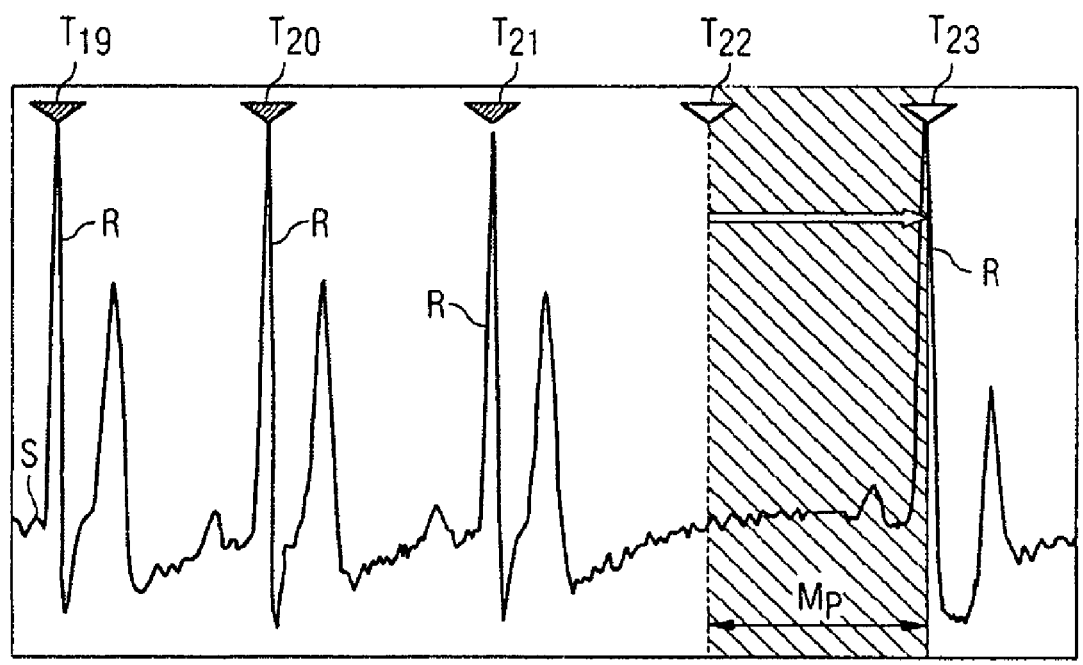
FIG. 4b shows a schematic illustration of a measurement time interval within an EKG with a delayed R-peak.

FIGS. 4a and 4b show examples of how the control device 10 and the computed tomography system 1 according to an embodiment of the invention can react when exceptional situations occur within the EKG. FIG. 4a in this case shows the case of an extrasystole. As illustrated here, this is evident in the EKG signal S by a premature, smaller R-peak appearing in addition to the systoles at the times $T_{15}$, $T_{16}$ and $T_{18}$ at the time $T_{17}$ rather than at the estimated time $T_{17}$. In this case, data recording preferably starts immediately during a measurement time interval $M_P$, which is continued until the next R-peak is detected at the time $T_{18}$. This ensures that the next heart cycle can also always be used for data recording.

FIG. 4b shows the situation when an R-peak occurs too late. In this case, the R-peaks in the EKG signal S initially occur at very uniform time intervals at the times $T_{19}$, $T_{20}$, $T_{21}$. On the basis of these timings, it is expected that the next R-peak will occur at the latest at the time $T_{22}$ in a time period. However, this actually does not occur until the time $T_{23}$. For this reason, a decision is made at the time $T_{22}$ not to end the data recording as calculated in advance but continue it during a measurement time interval $M_P$ until the next R-peak actually occurs at the time $T_{23}$, in order to additionally use this time period.

The method according to an embodiment of the invention has been examined on the basis of 420 EKGs in comparison to conventional spiral acquisitions using EKG-correlated tube current modulation. On the one hand, the measurement method according to the invention was compared with a spiral scanning method in this case, in which the remaining dose with tube-current modulation was still 20%, as is normal in most cases with EKG-correlated tube-current modulation.

In comparison to this method, a dosage reduction of 51% was achieved by the sequential method according to an embodiment of the invention. As an alternative, a comparison was also carried out with a spiral scanning method in which the tube current was reduced even further (down to 2%) which is equivalent to effectively completely shutting it down. A dosage reduction of 38% was still achieved in comparison to a "dosage-optimized" spiral scanning method such as this. In this case, the method according to an embodiment of the invention resulted in a total scanning time that was just as fast, or at most insignificantly slower, than the spiral scanning method. This indicates that the sequential method according to an embodiment of the invention can be used for measurement without any significant time loss and lengthening of the overall measurement time—even in the case of complicated irregular EKGs—resulting in considerable dosage savings in comparison to the spiral scanning methods which are otherwise used in situations such as these.

Finally, it should once again be noted that the computed tomography system described in detail above and the described methods represent only example embodiments which may be modified in widely differing ways by a person skilled in the art without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for imaging an organ in a human or animal body via a computed tomography system including an X-ray radiation source to rotate around the body along a circumferential ring, the method comprising:
   fixing the circumferential ring in one position for recording of an image data segment on one slice plane during one revolution of the X-ray radiation source relative to the body;
   triggering the X-ray radiation source by a cycle signal which represents a movement cycle of the organ, the X-ray radiation source being activated for a limited measurement time interval;
   moving the circumferential ring sequentially to further positions relative to the body between each of the recordings in order to record image data on further slice planes; and
   dynamically matching timing and duration of the measurement time interval for an image data segment to be recorded to a structure of the cycle signal at that time.

2. The method as claimed in claim 1, wherein a variable safety time interval, dependent on the structure of the cycle signal, is added in order to determine a measurement time interval for a subsequent measurement to form a minimum time interval which depends on the rotation rate of the X-ray radiation source and an angle range to be covered.

3. The method as claimed in claim 2, wherein the safety time interval is chosen as a function of the variability of the cycle signal at that time.

4. The method as claimed in claim 1, wherein, in order to define a start time for a subsequent measurement time interval, a time or a time period of the next occurrence of a specific characteristic feature in the cycle signal is estimated on the basis of the profile of previous signal cycles.

5. The method as claimed in claim 2, wherein at least one of the variable safety time interval is defined and the time of the next occurrence of the specific characteristic feature is estimated as a function of a at least one of a mean value and a median of the cycle length of a number of previous cycles.

6. The method as claimed in claim 2, wherein at least one of the variable safety time interval is defined and the time of the next occurrence of the specific characteristic feature is estimated as a function of one or more of the following parameters:
   minimum cycle length of a number of previous cycles,
   maximum cycle length of a number of previous cycles,
   trend line of the cycle length of a number of previous cycles, and
   standard deviation of the cycle length of a number of previous cycles.

7. The method as claimed in claim 2, wherein the safety time interval has a predeterminable minimum length.

8. The method as claimed in claim 1, wherein the image data recording is terminated if a specific characteristic feature occurs while an image data segment is being recorded.

9. The method as claimed in claim 4, wherein, if a specific characteristic feature occurs before an estimated earliest time of the next occurrence of the specific characteristic feature, the recording an image data segment is started.

10. The method as claimed in claim 4, wherein the feature does not occur at an estimated time or in an estimated time period of the next occurrence of the specific characteristic feature, the recording of an image data segment is started from a specific time.

11. The method as claimed in claim 1, wherein, after recording an image data segment, a check is carried out to determine whether a further image data segment should be recorded at the present position.

12. The method as claimed in claim 1, wherein the cycle signal is an EKG signal.

13. A control device for a computed tomography system for imaging an organ in a human or animal body, the system including an X-ray radiation source which rotates along a circumferential ring around the body, and a movement device in order to adjust the circumferential ring and the body relative to one another, the control device comprising:
   a signal input for inputting a cycle signal representing a movement cycle of the organ, the control device being designed to operate the computed tomography system such that the circumferential ring is fixed in one position for recording of an image data segment on one slice plane during one revolution of the X-ray radiation source relative to the body, the X-ray radiation source is triggered by the cycle signal and is activated for a limited measurement time interval, and the circumferential ring is moved sequentially to further positions along the body between each of the recordings in order to record image data on further slice planes; and a measurement time interval determining unit to dynamically match the timing and length of the measurement time interval for an image data segment to be recorded to a structure of the cycle signal at that time.

14. A computed tomography system for imaging an organ for a human or animal body, comprising:

an X-ray radiation source to rotate around the body along a circumferential ring;

a movement device to adjust the circumferential ring and the body relative to one another; and a control device as claimed in claim 13.

15. A computer program product which can be loaded directly into a memory of a control device of a computed tomography system, including program code segments in order to carry out all the steps of a method as claimed in claim 1 when the computer program product is run on the control device.

16. The method as claimed in claim 2, wherein, after recording an image data segment, a check is carried out to determine whether a further image data segment should be recorded at the present position.

17. The method as claimed in claim 2, wherein the cycle signal is an EKG signal.

18. The method as claimed in claim 2, wherein, in order to define a start time for a subsequent measurement time interval, a time or a time period of the next occurrence of a specific characteristic feature in the cycle signal is estimated on the basis of the profile of previous signal cycles.

19. A non-transitory computer readable medium including program segments for, when executed on a computer device, causing the computer device to implement the method of claim 1.

* * * * *